(12) United States Patent
D'Andrea et al.

(10) Patent No.: US 10,898,244 B2
(45) Date of Patent: Jan. 26, 2021

(54) PACKAGING FOR TROCHANTERIC FEMORAL NAIL TELESCOPING HEAD ELEMENT

(71) Applicant: DePuy Synthes Products, Inc., Raynham, MA (US)

(72) Inventors: Dominic D'Andrea, West Chester, PA (US); David Moszak, West Chester, PA (US); Andrew Flintrop, West Chester, PA (US); Dana Pappalardo, West Chester, PA (US); John Anastasiadis, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 64 days.

(21) Appl. No.: 16/192,889

(22) Filed: Nov. 16, 2018

(65) Prior Publication Data
US 2020/0155207 A1  May 21, 2020

(51) Int. Cl.
*A61B 17/74* (2006.01)
*A61B 17/88* (2006.01)
*A61B 17/86* (2006.01)
*A61B 17/92* (2006.01)
*A61F 2/30* (2006.01)

(52) U.S. Cl.
CPC ........ *A61B 17/744* (2013.01); *A61B 17/8872* (2013.01); *A61B 17/746* (2013.01); *A61B 17/8605* (2013.01); *A61B 17/92* (2013.01); *A61F 2/30739* (2013.01)

(58) Field of Classification Search
CPC ... A61B 17/744; A61B 17/8872; A61B 17/74; A61F 2/30739
See application file for complete search history.

(56) References Cited

U.S. PATENT DOCUMENTS

| 2,937,642 A | 5/1960 | Lange et al. |
| 3,107,666 A | 10/1963 | Cecere et al. |
| 4,106,620 A | 8/1978 | Brimmer et al. |
| 4,172,452 A | 10/1979 | Forte et al. |
| 5,133,765 A | 7/1992 | Cuilleron |

(Continued)

FOREIGN PATENT DOCUMENTS

| DE | 202014100438 | 4/2014 |
| JP | H0966060 | 3/1997 |
| WO | 2018/009401 | 1/2018 |

*Primary Examiner* — Ellen C Hammond
(74) *Attorney, Agent, or Firm* — Fay Kaplun & Marcin, LLP

(57) ABSTRACT

A system includes an implant and a packaging device assembled with the implant to hold an outer sleeve and a head element of the implant in a desired position relative to one another. The packaging device includes clip arms sized and shaped so that, when the arms are held toward a closed configuration, the implant is housed therebetween in the desired position and proximal ends of the arms form a space via which an insertion device is insertable to be coupled to the implant, and a housing defining a space within which the clip is housed. The housing includes a retaining feature for retaining the clip therein and a camming element which, when a proximal force is exerted on the implant via the insertion device coupled thereto, causes the arms to move away from one toward an open configuration to release the implant therefrom.

9 Claims, 2 Drawing Sheets

(56) References Cited

U.S. PATENT DOCUMENTS

| | | |
|---|---|---|
| 5,409,492 A | 4/1995 | Jones et al. |
| 5,507,762 A | 4/1996 | Abidin et al. |
| 6,880,699 B2 | 4/2005 | Gallagher |
| 7,617,932 B2 | 11/2009 | Windus-Smith et al. |
| 7,763,080 B2 | 7/2010 | Southworth |
| 8,808,293 B2 | 8/2014 | Buettler et al. |
| 2002/0156473 A1 | 10/2002 | Bramlet et al. |
| 2003/0221977 A1 | 12/2003 | Kumar et al. |
| 2013/0000262 A1* | 1/2013 | Richart .................. A61C 19/02 53/492 |
| 2017/0143449 A1 | 5/2017 | Zieris et al. |

* cited by examiner

PACKAGING FOR TROCHANTERIC FEMORAL NAIL TELESCOPING HEAD ELEMENT

BACKGROUND

Fractures are often treated with screws or other fixation devices inserted into the bone to stabilize portions thereof once they have been brought into corrective alignment. In particular, hip fractures (e.g., trochanteric fractures of the proximal femur) may be treated using proximal femoral nail systems including the insertion of an intramedullary nail into a medullary cavity of a long bone such as a femur and subsequent insertion of an implant into the femoral head angled relative to the intramedullary nail (e.g., along an axis of the femoral neck). In some cases, the implant may include a telescoping femoral head component to permit compression of the bone during healing.

SUMMARY

The present disclosure is directed to a system for treating a bone, comprising an implant including an outer sleeve and head element, the outer sleeve extending longitudinally from a proximal end to a distal end, the head element including a shaft and a bone-engaging portion at a distal end of the shaft, the shaft slidably received within the outer sleeve and longitudinally movable relative thereto, and a packaging device removably assembled with the implant to hold the outer sleeve and the head element in a desired position relative to one another. The packaging device includes a clip including a pair of clip arms extending from proximal ends to distal ends connected to one another, the clip arms sized and shaped so that, when the clip arms are held together toward a closed configuration, the implant is housed therebetween in the desired position and the proximal ends of the clip arms form a substantially cannular space via which an insertion device is insertable to be coupled to the implant housed therebetween, and a housing extending from a closed distal end to an open proximal end and defining a space within which the clip is housed, the housing including a retaining feature for retaining the clip therein and a camming element at the proximal end which, when a proximal force is exerted on the implant via an insertion device coupled thereto, causes the clip arms to move away from one another toward an open configuration to release the implant therefrom.

The present disclosure is also directed to a method for releasing an implant from a packaging device, comprising inserting an insertion device through a space defined between proximal ends of clip arms of a packaging device to couple the insertion device to a proximal end of an implant housed between the clip arms in a desired position, wherein the implant includes an outer sleeve and head element, the outer sleeve extending longitudinally from a proximal end to a distal end, the head element including a shaft and a bone-engaging portion at a distal end of the shaft, the bone engaging portion separated from the outer sleeve via a predetermined distance in the desired position, the clip arms housed within a housing which holds the clip arms toward a closed configuration, moving the insertion device and implant proximally relative to the housing such that the clip arms exert a proximal force on a camming element at the proximal end causing the clip arms to move away from one another toward an open configuration to release the implant from therebetween, and drawing the implant proximally out of the packaging device.

BRIEF DESCRIPTION

DETAILED DESCRIPTION

Figure 1:
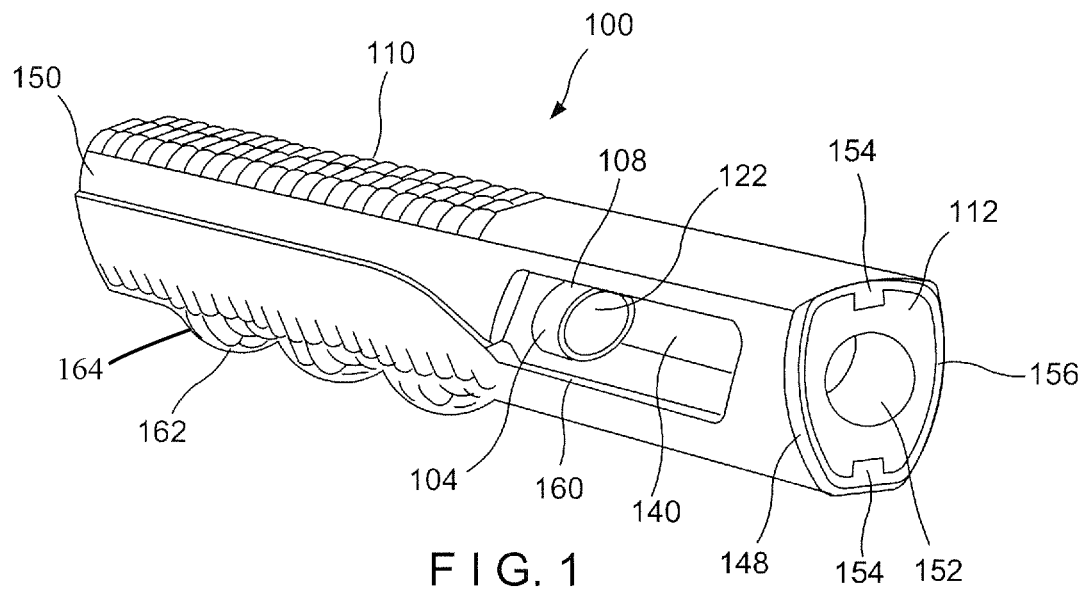
FIG. 1 shows a perspective view of a system according to an exemplary embodiment of the present disclosure.

The present disclosure may be further understood with reference to the following description and the appended drawings, wherein like elements are referred to with the same reference numerals. The present embodiments relate to the treatment of a bone and, in particular, to the treatment of fractures of long bones such as the femur, humerus, etc. Fracture of a long bone such as the femur may be treated using, for example, a proximal nailing system including an intramedullary nail insertable into a medullary canal of the femur and an implant insertable through the intramedullary nail into a head of the femur along an axis of the femoral neck. The implant may include a head element which telescopes with respect to an outer sleeve. The head element may be connected to the outer sleeve via, for example, a ratchet mechanism configured to allow the implant to collapse along its length over time. As would be understood by those skilled in the a rt, the ratchet mechanism is configured to permit compression of the fracture during healing while preventing medial migration of the head element toward the acetabulum. To ensure the implant is not damaged prior to insertion into the bone, the implant should be prevented from collapsing (contracting telescopically) prior to implantation. If the implant collapses prior to insertion, there is a risk that the ratchet mechanism may be damaged during insertion into the bone, under the force of hammering. If the ratchet mechanism breaks, the head element may become separated from the outer sleeve, permitting medial migration of the head element toward the acetabulum. The exemplary embodiments describe a packaging device for holding the head element and the outer sleeve of the implant in a desired position relative to one another during coupling of the implant to an insertion device. The packaging device comprises a clip specifically sized, shaped and configured to hold the head element and the outer sleeve in a desired position relative to one another between arms of the clip, when the arms of the clip are in a closed configuration. The arms of the clip are held in the closed configuration via a housing until an insertion device is coupled to the implant. Once the insertion device has been coupled to the implant, however, the insertion device, with the implant coupled thereto, may be drawn proximally relative to the housing so that a proximally directed force exerted on the implant causes a portion of the arms, within which the implant is housed, to interface with a portion of the housing so that the clip arms are opened, releasing the implant from the clip anus. It will be understood by those of skill in the art that the terms proximal and distal, as used herein refer to a direction toward (proximal) and away from (distal) a user of the system described herein. It will be further understood that, although the embodiments described herein are directed to the femur, systems for treating other long bones such as the humerus may be substantially similarly constructed.

Figure 2:
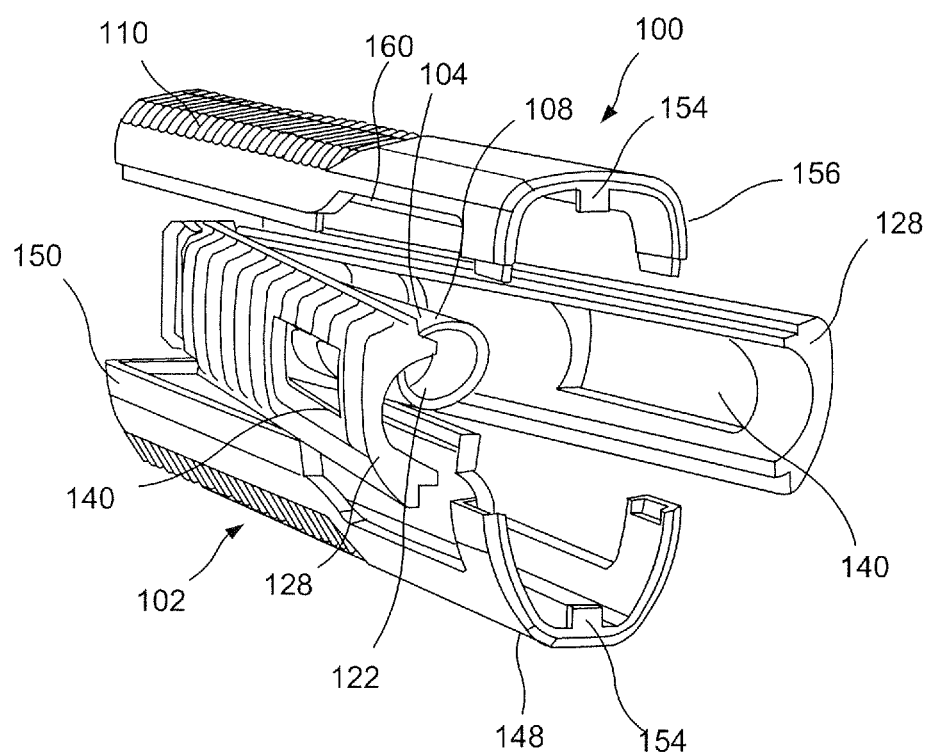
FIG. 2 shows an exploded perspective view of the system of FIG. 1.
Figure 3:
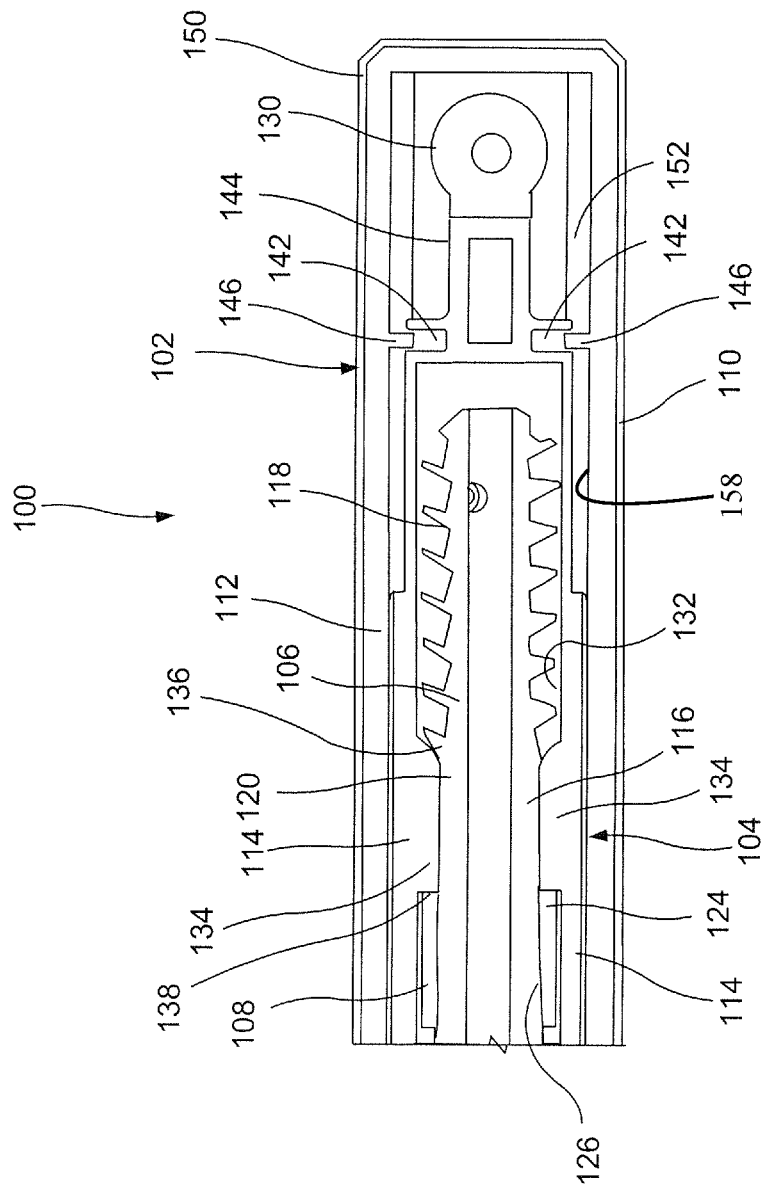
FIG. 3 shows a longitudinal cross-sectional view of the system of FIG. 1.

As shown in FIGS. 1-3, a system 100 comprises a packaging device 102 for holding an implant 104 in a desired configuration during coupling of the implant 104 to an insertion device. The implant 104 is configured to be inserted through an intramedullary nail and into a head portion of a bone (e.g., femur) and, as would be understood by those skilled in the art, the implant may be inserted into the bone via hammer blows to a proximal end of the insertion device. The implant 104 includes a head element 106 and an outer sleeve 108 connected to one another via, for example, a ratchet mechanism configured to allow the implant 104 to collapse along its length (shorten) while preventing the implant 104 from lengthening so that a distal end of the implant does not migrate medially. The packaging device 102 includes a housing 110 within which a clip 112 is housed. The clip 112 includes arms 114 sized, shaped and configured to hold the head element 106 and the outer sleeve 108 in a desired position relative to one another between the arms 114, so long as the arms 114 are held in a closed configuration via the housing 110. In particular, the arms 114 may be specifically molded so that the shapes of the anus 114, when held together, correspond to a shape of the implant 104 with the head element 106 and the outer sleeve 108 in the desired position relative to one another. As will be described in further detail below, the implant 104 is held in the desired position via the clip 112 and the housing 110 until the insertion device has been coupled to the implant 104.

The implant 104 includes the head element 106 and the outer sleeve 108 while the head element 106 includes a longitudinally extending shaft 116 and a bone-engaging element 118 at a distal end 120 thereof. The shaft 116 is sized and shaped to be slidably received within a channel 126 of the outer sleeve 108, which extends longitudinally from a proximal end 122 to a distal end 124. The proximal end 122 of the outer sleeve 108 may be beveled so that, when the implant 104 is inserted through the intramedullary nail and into the head portion of the bone at an angle relative to a longitudinal axis of the intramedullary nail (e.g., parallel to an axis of the femoral neck), the proximal end 122 is flush with an exterior surface of the intramedullary nail or is received within the intramedullary nail. As described above, the shaft 116 of the head element 106 and the channel 126 of the outer sleeve 108 may engage one another via, for example, a ratchet mechanism which permits proximal (lateral) movement of the head element 106 relative to the outer sleeve 108 while preventing distal (medial) movement of the head element 106 relative to the outer sleeve 108. The bone-engaging element 118 has a cross-sectional area larger than a cross-sectional area of the shaft 116 and may have any of a variety of bone-engaging features such as, for example, threading or helical blades as would be understood by those skilled in the art.

The packaging device 102 in this embodiment is pre-assembled with the implant 104 during manufacturing to prevent the implant 104 from collapsing prior to insertion of the implant 104 into the bone. As described above, the packaging device 102 includes the housing 110 and the clip 112. The clip 112 includes the pair of arms 114 which are sized, shaped and configured so that, when the arms 114 are held toward one another in a closed configuration, the implant 104 is housed therebetween maintaining the head element 106 and the outer sleeve 108 in the desired position relative to one another and preventing collapse of the implant 104. Each of the arms 114 extends from a proximal end 128 to a distal end 130, the distal ends 130 of the arms 114 are connected to one another so that the arms 114 may be moved from the closed configuration toward an open configuration in which the proximal ends 128 of the arms 114 are separated from one another to release the implant 104 held therebetween. The arms 114 are shaped so that, even when the arms 114 are in the closed configuration, the arms 114 define a cannular space 138 through which the insertion device may be inserted to be coupled to the implant 104.

An interior surface 132 of the arms 114 of this embodiment includes a protrusion 134 extending radially inward, with the protrusion 134 being sized and shaped so that, when the implant 104 is held between the arms 114 in the closed configuration, the protrusion 134 is interposed between a proximal end 136 of the bone engaging portion 118 of the head element 106 and a distal end 124 of the outer sleeve 108 to hold the head element 106 and the outer sleeve 108 in a desired position relative to one another.

A proximal portion of each of the arms 114 of this embodiment also includes an optional window 140 extending laterally through the arms 114 so that a coupling of the insertion device to the implant 104 is visible to a user via the window 140. Thus, the proximal end 122 of the outer sleeve 108 may extend proximally of a distal end 142 of the window 140. Although the exemplary embodiment shows and describes each of the arms 114 as including a window 140, it will be understood by those of skill in the art that it is also possible for just one of the arms 114 to include the window 140. Having a window 140 extending through each of the arms 114 will, however, allow a user to visualize the coupling of the insertion device to the implant 104 regardless of an orientation of the packaging device 102 during coupling.

A distal portion of the arms 114 may also include a retention feature configured to retain the clip 112 within the housing 110 when the implant 104 is being removed therefrom. In one embodiment, the retention feature may be configured as a groove 142 extending into an exterior surface 144 of the clip arms 114 proximate the distal end 130 for receiving a correspondingly shaped tab 146 of the housing 110. The groove 142 and the tab 146 engage one another so that the clip 112 is prevented from being drawn proximally out of the housing 110 during release of the implant 104 therefrom.

The housing 110 extends longitudinally from an open proximal end 148 to a closed distal end 150 to define an interior space 152 sized and shaped to house the clip 112 therein. The proximal end 148 includes a pair of camming elements 154 extending radially inward from a proximal face 156 of the housing 110 so that the camming elements 154 extend proximally beyond at least a portion of the proximal ends 128 of the arms 114. The camming elements 154 of this embodiment are substantially diametrically opposed to one another and positioned relative to the clip 112 such that each of the camming elements 154 extends between the clip arms 114. Thus, once the insertion device 102 has been coupled to the implant 104, the insertion device 102, and thereby the implant 104, may be drawn proximally relative to the housing 110 so that a proximal force of the clip 112 against the camming elements 154 moves the clip arms 114 away from another toward the open configuration, to release the implant 104 from therebetween.

As described above, the housing 110 also includes tabs 146 extending inward from an interior surface 158 thereof for engaging the grooves 142. A distance via which the tabs 146 extend into the interior space 152, however, is smaller than a depth of the grooves 142 so that, as the clip arms 114 are moved toward the open configuration—i.e. arms 114 are moved toward the interior surface 158 of the housing 110—there is sufficient room for the tabs 146 to be received deeper within the grooves 142 so that the clip 112 remains engaged to the housing 110 and is prevented from being proximally removed therefrom.

A proximal portion of the housing 110 may also include windows 160 corresponding in size, shape and position to the windows 140 of the clip 112 to maintain visibility of the interior of the packaging device 102 during coupling of the insertion device to the implant 104. A distal portion of the housing 110 may include finger grips 162 along an exterior surface 164 thereof to facilitate gripping of the packaging device 102 during coupling of the insertion device to the implant 104 and a subsequent removal of the implant 104 from the packaging device 102.

As described above, the implant 104 may be preassembled with the packaging device 102 to hold the head portion 106 and the outer sleeve 108 of the implant 104 in a desired position relative to one another to prevent premature collapse of the implant 104 prior to insertion. In this preassembled configuration, the clip 112 is housed within the housing 110 in the closed configuration, so that the implant 104 is held between the arms 114 in the desired configuration. To prepare the implant 104 for implantation into the bone, as described above, the user may insert the insertion device through the cannular space 138 of the arms 114 of the clip 112 housed within the housing 110 to couple a distal end of the insertion device 102 with the implant 104, as will be understood by those of skill in the art. The user may visualize a coupling of the insertion device with the implant 104 via the windows 140, 160 to ensure that the insertion device is coupled to the implant 104 in a correct alignment therewith.

It will be understood by those of skill in the art that the head portion 106 and the outer sleeve 108 maintain their desired relative positions upon coupling of the insertion device to the implant 104. Thus, upon coupling of the insertion device with the implant 104, the user may draw the insertion device, and thereby the implant 104, proximally with respect to the housing 110 to remove the implant 104 from the packaging device 102. Since the clip 112, as described above, is sized and shaped to correspond to a shape of the implant 104, drawing the implant 104 proximally also applies a proximal force to the clip 112. The proximal force of the clip 112 against the caroming elements 154 of the housing 110 opens the clip arms 114 so that the implant 104 may be drawn proximally therefrom. In particular, the arms 114 of the clip 112 are spread far enough apart so that the bone engaging portion 118 of the head portion 106 of the implant 104 is able to move proximally past the protrusion 134 and out of the packaging device 102. As described above, the retention feature—e.g., the groove 142 of the clip 112 and the tab 146 of the housing 110—retains the clip 112 within the housing 110 so that, as the arms 114 are moved toward the open configuration, the implant 104 may be drawn proximally out of the packaging device 102.

It will be understood by those of skill in the art that modifications and variations may be made in the structure and methodology of the present invention, without departing from the spirit and scope of the invention. Thus, it is intended that the present invention cover the modifications and variations of this invention, provided that they come within the scope of the appended claims and their equivalents.

What is claimed is:

1. A method for releasing an implant from a packaging device, comprising:
    inserting an insertion device through a space defined between proximal ends of clip arms of a packaging device to couple the insertion device to a proximal end of an implant housed between the clip arms in a desired position, wherein the implant includes an outer sleeve and head element, the outer sleeve extending longitudinally from a proximal end to a distal end, the head element including a shaft and a bone-engaging portion at a distal end of the shaft, the bone engaging portion separated from the outer sleeve via a predetermined distance in the desired position, the clip arms housed within a housing which holds the clip arms toward a closed configuration;
    moving the insertion device and implant proximally relative to the housing such that the clip arms exert a proximal force on a caroming element at a proximal end of the housing causing the clip arms to move away from one another toward an open configuration to release the implant from therebetween; and
    drawing the implant proximally out of the packaging device.

2. The method of claim 1, wherein drawing the implant proximally out of the packaging device includes moving the bone engaging portion of the implant proximally past a protrusion extending laterally inward from an interior surface of the clip arms, the protrusion sized and shaped to be received between a proximal end of the bone-engaging portion and the distal end of the outer sleeve to hold the outer sleeve and the head element in the desired position relative to one another when the clip arms are in the closed configuration.

3. The method of claim 1, wherein the clip arms are retained within the housing during release of the implant therefrom via a retaining feature.

4. The method of claim 3, wherein the retaining feature includes a tab extending radially inward from an interior surface of the housing and engaging a corresponding groove along a distal portion of the clip arms.

5. The method of claim 4, wherein, when the clip arms are moved from the closed configuration toward the open configuration, the tab is received deeper within the groove to maintain a retention of the clip within the housing.

6. The method of claim 1, wherein inserting the insertion device between the proximal ends of the clip arms includes visualizing a coupling of the insertion device to the implant via a window extending laterally through a proximal portion of the clip arms.

7. The method of claim 6, wherein a proximal portion of the housing includes a window extending laterally therethrough, the window of the housing corresponding in size, shape and position to the window of the clip arms.

8. The method of claim 1, wherein the camming element extends radially inward from a proximal face of the housing so that the camming element extends proximally of at least a portion of the proximal ends of the clip arms.

9. The method of claim 1, further comprising gripping the housing via gripping features along a distal portion of an exterior surface thereof to facilitate one of inserting the insertion device between the clip arms and drawing the implant proximally out of the packaging device.

* * * * *

UNITED STATES PATENT AND TRADEMARK OFFICE
CERTIFICATE OF CORRECTION

PATENT NO. : 10,898,244 B2
APPLICATION NO. : 16/192889
DATED : January 26, 2021
INVENTOR(S) : D'Anrea et al.

It is certified that error appears in the above-identified patent and that said Letters Patent is hereby corrected as shown below:

In the Claims

Claim 1, Column 6, Line 19:
"proximal force on a caroming element at a proximal" should read "proximal force on a camming element at a proximal".

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*